United States Patent [19]

Tanaka et al.

[11] Patent Number: 4,951,670
[45] Date of Patent: Aug. 28, 1990

[54] NON-CONTACT EYE PRESSURE METER

[75] Inventors: Shinya Tanaka, Tokyo; Koichi Yano, Kawasaki, both of Japan

[73] Assignee: Canon Kabushiki Kaisha, Tokyo, Japan

[21] Appl. No.: 161,168

[22] Filed: Feb. 26, 1988

[30] Foreign Application Priority Data

Mar. 6, 1987 [JP] Japan ................................ 62-51784

[51] Int. Cl.⁵ .............................................. A61B 3/16
[52] U.S. Cl. .................................... 128/648; 128/652
[58] Field of Search ...................... 128/645, 648, 652

[56] References Cited

U.S. PATENT DOCUMENTS 3,585,849  6/1971  Grolman .
3,832,890  9/1974  Grolman et al. ................. 128/648
3,882,718  5/1975  Kriebel .............................. 128/648
4,724,843  2/1988  Fisher ................................ 128/648
4,770,181  9/1988  Tomoda ............................ 128/648

FOREIGN PATENT DOCUMENTS 183621    6/1986  European Pat. Off. ........... 128/648
54-38437  11/1979  Japan .
59-143402  9/1984  Japan .

Primary Examiner—Max Hindenburg
Assistant Examiner—J. P. Lacyk
Attorney, Agent, or Firm—Fitzpatrick, Cella, Harper & Scinto

[57] ABSTRACT

In a non-contact eye pressure meter wherein the cornea of an eye to be examined is pressurized to thereby detect predetermined deformation of the cornea of the eye to be examined and find the eye pressure value, the interim cornea deformation before said predetermined deformation of the cornea of the eye to be examined is detected, whereafter the degree of pressurization to the cornea of the eye to be examined is reduced.

15 Claims, 5 Drawing Sheets

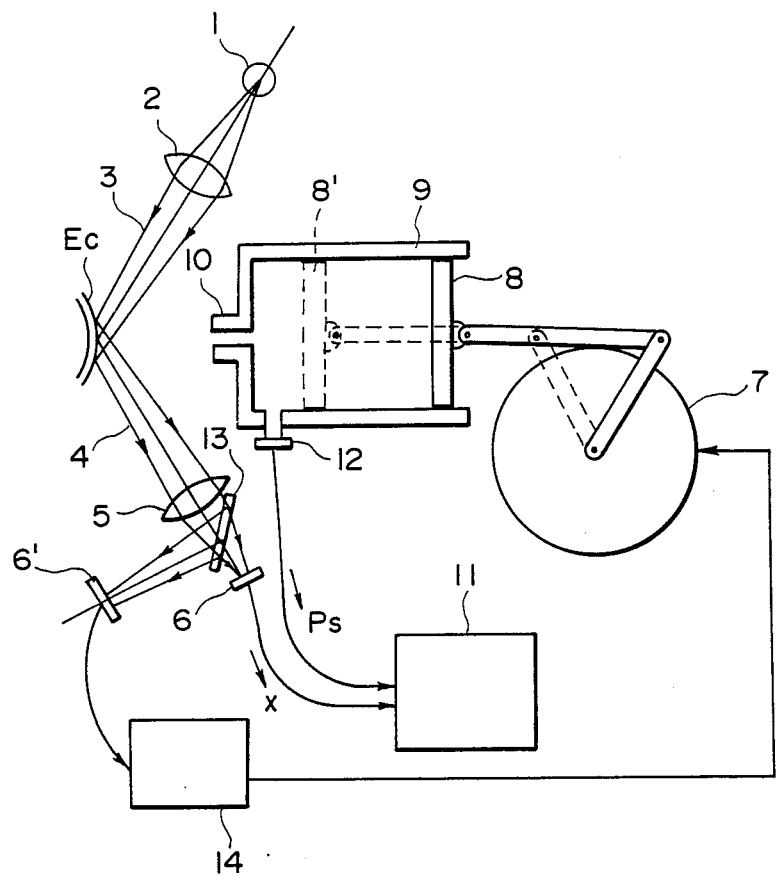
F I G. I

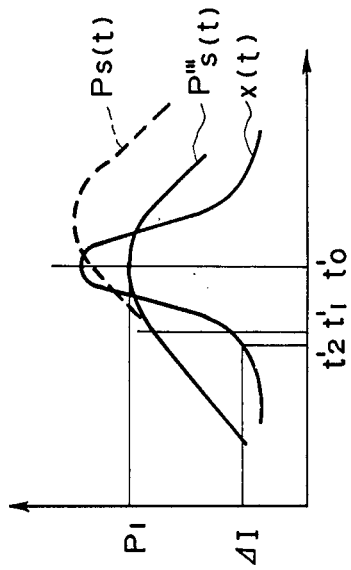
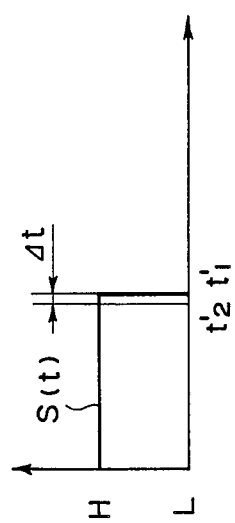
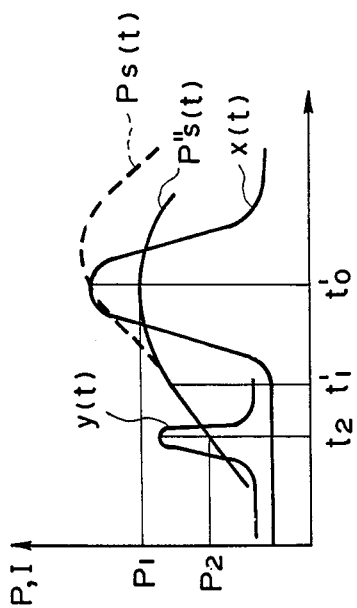
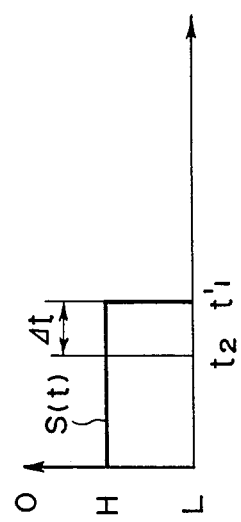
FIG. 2(a)
FIG. 2(b)
FIG. 3(a)
FIG. 3(b)

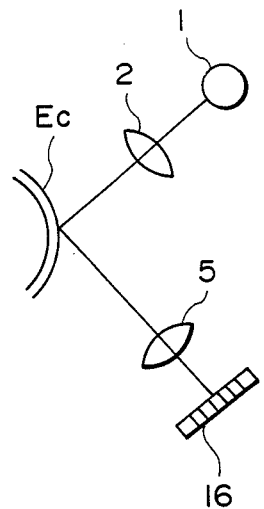
F I G. 4
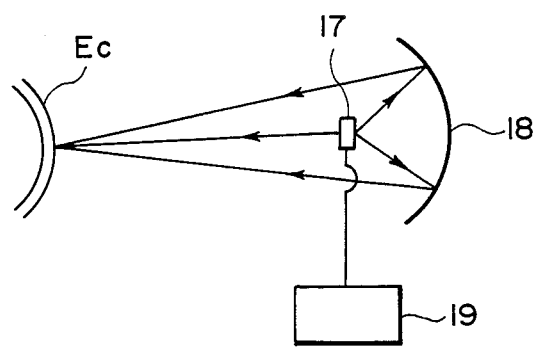
F I G. 5

NON-CONTACT EYE PRESSURE METER

BACKGROUND OF THE INVENTION

1. Field of the Invention

This invention relates to a non-contact eye pressure meter for pressurizing the cornea of an eye to be examined in a non-contact fashion to thereby detect predetermined deformation of the cornea and find the eye pressure value, and in particular to an apparatus in which the pressure applied to the eye to be examined is reduced to the necessary minimum, whereby the examinee's sense of discomfort is mitigated.

1. Related Background Art

Non-contact eye pressure meters in which fluid is emitted to the cornea of an eye to be examined and the predetermined deformation (planar surface) of the cornea by this fluid is detected to thereby find the eye pressure value are known, for example, from Japanese Patent Publication No. 38437/1979 and Japanese Laid-Open Utility Model Application No. 143402/1984. Describing the apparatus of Japanese Laid-Open Utility Model Application No. 143402/1984 as an example, this known apparatus, as shown in FIG. 6 of the accompanying drawings, is comprised of a cornea deformation detecting system in which a light emitted from a light source 1 passes through a lens 2 to provide a measuring light beam 3 which travels to the cornea E of an eye to be examined and the reflected light beam 4 reflected thereby is caused by a lens 5 to enter a light-receiving element 6, and an air pulse generating system in which a piston 8 is pushed by the rotation of a rotary solenoid 7 and the air in a cylinder 9 is compressed, whereby an air stream with its pressure variable with time is emitted from a nozzle 10 toward the cornea of the eye to be examined. There are further provided a pressure sensor 12 for measuring the pressure in the cylinder 9 and a processing circuit 11 connected to the light-receiving element 6 and the pressure sensor 12, and the cylinder internal pressure signal when the cornea deformation detecting system detects the predetermined deformed state of the cornea is measured and converted into the eye pressure of the eye to be examined. In the prior art apparatus of this type, the driving of the solenoid 7 is stopped usually after the predetermined deformation of the cornea is detected, and the load by excess air pulse is prevented from being applied to the eye to be examined. FIGS. 7(a) and 7(b) of the accompanying drawings show that state. The output x(t) of the light-receiving element 6 and the output Ps(t) of the pressure sensor 12 are both shown in FIG. 7(a), and the driving signal of the solenoid is shown in FIG. 7(b). The processing circuit 11 detects the peak of the output x(t) of the light-receiving element 6 at $t=t_0$, detects that predetermined deformation has been created in the cornea of the eye to be examined, and reads a cylinder internal pressure signal $P_1$, whereafter it renders a solenoid driving signal S(t) into a low level at $t=t_1$ after a slight predetermined processing time $\Delta t$ and stops the driving of the solenoid 7. Along therewith, the pressure in the cylinder 9 decreases and becomes as indicated by Ps(t) in FIG. 7(a). In FIG. 7(a), P's(t) shows the variation in the cylinder internal pressure when the driving of the solenoid is not stopped, and Ps(t) has a low peak as compared with P's(t) and the pressure of the air pulse emitted to the cornea of the eye to be examined is reduced.

However, in the above-described example of the prior art, the stoppage of the driving of the solenoid is effected after the detection of the predetermined deformation of the cornea and therefore, generation of excess air pulse cannot be completely eliminated and thus, the shock applied to the eye to be examined during measurement has not been sufficiently weak.

The eye pressure measurement by the apparatus of this type is usually effected three to five times and the representative value is adapted as the eye pressure of the eye to be examined, but the eye pressure value is much affected by the examinee's psychological condition. Accordingly, there has been the problem that if the shock of the air pulse during measurement is great, stable measurement cannot be accomplished in the second and subsequent measurements and a highly reliable measured value cannot sometimes be obtained.

SUMMARY OF THE INVENTION

It is an object of the present invention to provide a non-contact eye pressure meter in which the pressure applied to an eye to be examined is minimized to thereby mitigate the examinee's sense of discomfort.

It is also an object of the present invention to provide a non-contact eye pressure meter in which, for an eye to be examined having a low eye pressure, the examinee's sense of discomfort can be more mitigated.

BRIEF DESCRIPTION OF THE DRAWINGS

FIG. 1 shows an embodiment of an eye pressure meter according to the present invention.

FIGS. 2(a) and 2(b) are graphs illustrating the eye pressure measuring operation.

FIGS. 3(a) and 3(b) are graphs illustrating the eye pressure measuring operation of a different embodiment.

FIG. 4 shows a different embodiment of the cornea deformation detection.

FIG. 5 shows a modification using an ultrasonic wave as a pressurizing system.

DESCRIPTION OF THE PREFERRED EMBODIMENTS

Figure 6:
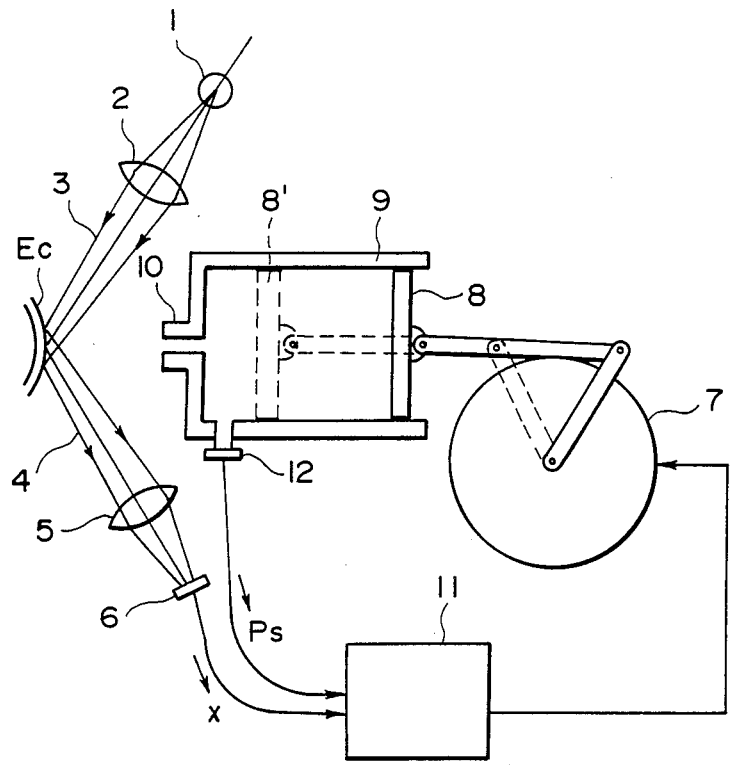
FIG. 6 shows an apparatus according to the prior art.
Figure 7A:
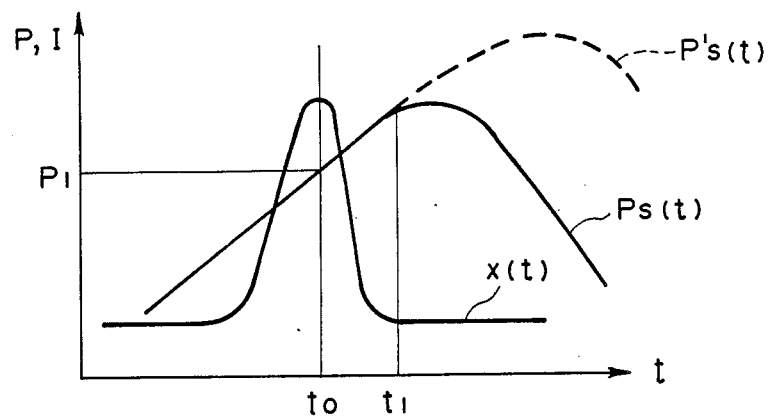
FIGS. 7(a) and 7(b) are graphs illustrating the eye pressure measuring operation of the prior art apparatus.
Figure 7B:
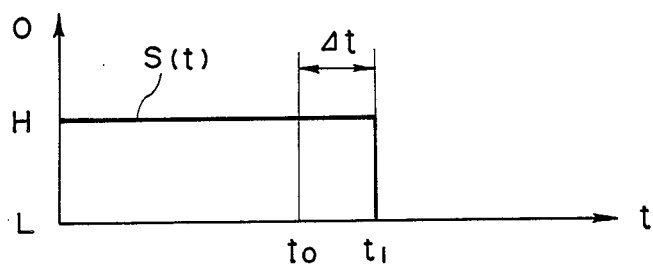

Referring to FIG. 1 which shows an embodiment of a non-contact eye pressure meter according to the present invention, a light distributor 13 is provided rearwardly of the lens 5 of the cornea deformation detecting system of the prior art apparatus shown in FIG. 6, and a second light receptor 6' is provided in the direction of reflection of the light distributor 13. The output y(t) of the second light receptor 6' shown in FIG. 2(a) is designed so as to have a peak when the cornea of an eye to be examined assumes a cornea-deformed state created before the cornea-deformed state detected by a first light receptor 6. That is, the second light receptor 6' is provided on the optic axis of a lens 5 at a point farther from the cornea than the first light receptor 6. The output y(t) is input to a control circuit 14 for controlling the driving of an air pulse generating system, and the control circuit 14 detects the peak of the output y(t) and stops the driving of a solenoid 7. In FIG. 1, members given reference numerals similar to those in FIG. 6 are functionally similar to the members of the prior art apparatus of FIG. 6.

The operation of the present embodiment will now be described. When an air pulse is emitted from the air pulse generating system to the cornea of the eye to be examined, outputs x(t) and y(t) shown in FIG. 2(a) are obtained from the light receptors 6 and 6', respectively. The control circuit 14 detects the peak of the output y(t) of the light receptor 6' at $t=t_2$, detects that a first deformed state has been created in the cornea of the eye to be examined, renders a solenoid driving signal S(t) into a low level at $t=t'_1$ after a predetermined processing time $\Delta t$ as shown in FIG. 2(b), and stops the driving of the solenoid 7. Along therewith, the pressure P"s(t) in a cylinder 9 varies as shown in FIG. 2(a). That is, a piston 8 still continues to move from its inertia after the driving signal S(t) for the solenoid 7 has reached the low level and the pressure continues to slowly rise until it reaches a level somewhat higher than the pressure at $t=t'_1$. The output x(t) of the light receptor 6 has its peak at $t=t'_0$ when a second deformed state (the original deformed state for eye pressure measurement) of the cornea is created by the pressure rise thereafter, and a processing circuit 11 reads a cylinder internal pressure signal $P_1$ at this point of time and converts it into an eye pressure value.

In the previous embodiment, the driving of the solenoid is stopped irrespective of the eye pressure of the eye to be examined, in the predetermined time $\Delta t$ after the creation of the peak of the output y(t) of the light receptor 6' for the detection of the second cornea deformation. $\Delta t$ naturally includes the processing time required for the detection of the peak and in addition, has the meaning of ensuring the slow rise of the cylinder internal pressure after the driving of the solenoid is stopped. This is because if the rise of the pressure in the cylinder is insufficient, it becomes impossible to cause the second deformation for eye pressure measurement to be created in the cornea of the eye to be examined. The amount of pressure rise necessary for eye pressure measurement differs depending on the eye pressure of the eye to be examined, and to obtain the effect of the present invention sufficiently, it is desirable to vary this amount of pressure rise as a function of the eye pressure of the eye to be examined. However, except for a case where there is the past eye pressure data, it is impossible to know the eye pressure of the eye to be examined in advance and therefore, the following processing is carried out. The cylinder internal pressure signal $P_2$ at the time $t=t_2$ when the peak of the output y(t) of the light receptor 6' is created is read, and $\Delta t$ is set so as to be made great when $P_2$ is high with $\Delta t$ as a function of $P_2$, and so as to be made small when $P_2$ is low. Seemingly it is possible to measure the eye pressure by a very weak air pulse if the cylinder internal pressure signal $P_2$ is intactly utilized for eye pressure measurement, but in fact, the deformation of the cornea detected by the light receptor 6' is a very incipient state of deformation and therefore, stable measurement is impossible for the reasons such as the influence of the rigidity or the like of the eyeball and the very small difference from the initial shape before the deformation.

Also, in the previous embodiment, in order to detect the initial deformed state of the cornea of the eye to be examined, the second light receptor 6' has been used separately from the first light receptor 6 for detecting the cornea deformation from which the eye pressure value is calculated, but it is also possible to utilize the output signal x(t) of the first light receptor 6 without providing the second light receptor 6'. For example, the rising of the peak of the signal of the output x(t) of the light receptor 6 can be detected so that the driving of the solenoid may be stopped. That is, there may be provided a circuit for detecting that as shown in FIG. 3(a), the output x(t) of the light receptor 6 has increased by $\Delta I$ within a predetermined time from the initial state, and the driving of the solenoid may be stopped at $t=t'_1$ in the time $\Delta t$ after $t=t'_2$ when the rising thereof has been detected. If such a construction is adopted, an electric circuit will be the only member that must be newly added to the prior art apparatus of FIG. 6 and thus, not only it is possible to achieve the objects of the present invention very inexpensively, but also such a circuit only requires a very short processing time as compared with a peak detecting circuit, and measurement can be completed by a weaker air pulse.

Also, as shown in FIG. 4, the first and the second cornea deformation may of course be detected by a light position detecting element 16 (for example, a one-dimensional position detector). In such case, the position of the cornea-reflected light on the element differs in conformity with cornea deformation.

In the above-described embodiment, fluid is used as the pressurizing system, but alternatively, an ultrasonic wave may be used as shown in FIG. 5. In FIG. 5, the reference numeral 17 designates an ultrasonic wave vibrator, the reference numeral 18 denotes a concave mirror, and the reference numeral 19 designates an electrical input part. Also, in addition to stopping the solenoid to thereby reduce the degree of pressurization, the operation of the solenoid may be dulled to thereby reduce the degree of pressurization. Also, the pressure sensor 12 may desirably be one which measures the difference between the pressure in the cylinder 9 and the atmospheric pressure.

As described above, according to the present invention, a non-contact eye pressure meter which imparts less shock to the eye to be examined can be provided by a simple construction in which the initial deformed state of the cornea of the eye to be examined is detected to thereby control the operation of the pressurizing system. That is, measurement is completed by weaker pressurization and also, the point of time $t'_0$ at which the cornea deformation used for eye pressure measurement is created is $t_0 < t'_0$ relative to $t_0$ in the prior art apparatus and exhibits a gentle rise in the vicinity of the pressure peak, and this leads to the effect that the examinee feels the pressure more softly.

We claim:
1. A non-contact tonometer comprising:
non-contact pressurizing means for deforming a cornea of an eye to be examined by applying pressure, the intensity of which becomes larger with time, thereto;
first cornea deformation detecting means for detecting a first degree of cornea deformation;
calculating means for calculating intraocular pressure based on said first degree of cornea deformation detected by said first cornea deformation detecting means;
intermediate second cornea deformation detecting means for detecting a second degree of cornea deformation before the first degree of cornea deformation of the eye to be examined, said second degree of cornea deformation being less than said first degree of cornea deformation; and
control means for reducing the degree of pressurization of said pressurizing means after said second cornea deformation detecting means detects said second degree of cornea deformation before said first degree of cornea deformation.

2. A non-contact tonometer according to claim 1, wherein said pressurizing means includes a fluid projection means.

3. A non-contact tonometer according to claim 1, wherein said pressurizing means includes an ultra-sonic projection means.

4. A non-contact tonometer according to claim 1, wherein each of said first and second cornea deformation detecting means are provided with light detecting means, wherein said light detecting means of said first and second cornea deformation detecting means are independent of each other.

5. A non-contact tonometer according to claim 4, wherein said first and intermediate second cornea deformation detecting means are provided with a common light source for irradiating the cornea, and wherein said a light detecting means of said first and second cornea deformation detecting means detect the quantity of the light reflected by the cornea, said light detecting means are provided at different positions in the optical axis.

6. A non-contact tonometer according to claim 2, wherein said pressurizing means is provided with a cylinder for compressing fluid, a piston and a solenoid for driving the piston, and said control means stops the driving of said solenoid when said second cornea deformation detecting means detects said intermediate second degree of cornea deformation.

7. A non-contact tonometer according to claim 6, wherein said control means stops the driving of said solenoid at upon the expiration of a predetermined time after said intermediate second deformation detecting system detects said second degree of cornea deformation.

8. A non-contact tonometer according to claim 7, wherein said predetermined time is established irrespective of the intraocular pressure of the eye to be examined.

9. A non-contact tonometer according to claim 7, wherein said predetermined time is determined as a function of the intraocular pressure of the eye to be examined.

10. A non-contact tonometer according to claim 9, wherein said predetermined time is set on the basis of the pressure of said pressurizing means when said intermediate second deformation detecting system detects said second degree of cornea deformation.

11. A non-contact tonometer according to claim 1, further comprising a pressure sensor for measuring the pressure of said pressurizing means when said first deformation detecting means detects said first degree of cornea deformation, said pressure sensor connected to said pressurizing means, wherein said calculating means calculates the eye pressure value of the eye to be examined on the basis of the output of said pressure sensor.

12. A non-contact tonometer according to claim 11, wherein said pressure sensor measures the difference in value between the pressure in said pressurizing system and the atmospheric pressure.

13. A non-contact tonometer comprising:
non-contact pressurizing means for deforming the cornea of an eye to be examined by applying pressure, the intensity of which becomes larger with time, thereto;
cornea deformation detecting means for detecting first and second degrees of cornea deformation, said second degree of cornea deformation being less than said first degree of cornea deformation;
calculating means for calculating intraocular pressure based on said first degree of cornea deformation detected by said cornea deformation detecting means; and
control means for reducing the degree of pressurization of said pressurizing means after said cornea deformation detecting means detects the second degree of cornea deformation before said first degree of cornea deformation.

14. A non-contact tonometer according to claim 13, wherein said cornea deformation detecting means is provided with a light source for irradiating the cornea and light detecting means for detecting the quantity of the light reflected by the cornea, and said cornea deformation detecting means detects the second degree of cornea deformation when the output of said light detecting means exceeds a first level and detects said first degree of cornea deformation when the output of said light detecting means reaches a second level.

15. A non-contact tonometer according to claim 13, wherein said cornea deformation detecting system is provided with a light source for irradiating the cornea and light position detecting means for detecting the position of the light reflected by the cornea.

* * * * *

UNITED STATES PATENT AND TRADEMARK OFFICE
CERTIFICATE OF CORRECTION

PATENT NO. : 4,951,670
DATED : August 28, 1990
INVENTOR(S) : SHINYA TANAKA, ET AL.

It is certified that error appears in the above-identified patent and that said Letters Patent is hereby corrected as shown below:

COLUMN 1

Line 28, "cornea E" should read -- cornea Ec --.

COLUMN 4

Line 67, "second" should read --intermediate second--.

COLUMN 5

Line 10, "second" should read -- intermediate second --.
Line 13, "second" should read -- intermediate second --.
Line 19, "second" should read -- intermediate second --.
Line 19, "a" should be deleted.
Line 21, "cornea," should read -- cornea and --.
Line 22, "in the" should read --on an--.
Line 27, "second" should read -- intermediate second --.
Line 28, "intermediate" should be deleted.
Line 32, "at" should be deleted.

Signed and Sealed this

Sixth Day of April, 1993

*Attest:*

STEPHEN G. KUNIN

*Attesting Officer*       Acting Commissioner of Patents and Trademarks